(12) United States Patent
Zhang et al.

(10) Patent No.: US 10,209,390 B2
(45) Date of Patent: Feb. 19, 2019

(54) MEASURING FLUID CONDUCTIVITY

(71) Applicants: Wei Zhang, Houston, TX (US); Lizheng Zhang, Humble, TX (US); Li Gao, Katy, TX (US); Burkay Donderici, Houston, TX (US)

(72) Inventors: Wei Zhang, Houston, TX (US); Lizheng Zhang, Humble, TX (US); Li Gao, Katy, TX (US); Burkay Donderici, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 63 days.

(21) Appl. No.: 14/889,977

(22) PCT Filed: Aug. 5, 2013

(86) PCT No.: PCT/US2013/053550
§ 371 (c)(1),
(2) Date: Nov. 9, 2015

(87) PCT Pub. No.: WO2015/020624
PCT Pub. Date: Feb. 12, 2015

(65) Prior Publication Data
US 2016/0178788 A1 Jun. 23, 2016

(51) Int. Cl.
*G01V 3/38* (2006.01)
*G01N 27/06* (2006.01)
(Continued)

(52) U.S. Cl.
CPC .............. *G01V 3/38* (2013.01); *E21B 49/088* (2013.01); *G01N 27/023* (2013.01); *G01N 27/06* (2013.01);
(Continued)

(58) Field of Classification Search
CPC . G01V 3/38; G01V 3/28; G01N 27/06; G01N 27/08; G01N 49/088; G01N 33/2823; E21B 49/088; E21B 2049/085
See application file for complete search history.

(56) References Cited

U.S. PATENT DOCUMENTS 3,396,331 A 8/1968 Sperry, III
3,404,336 A 10/1968 Rosenthal
(Continued)

FOREIGN PATENT DOCUMENTS

GB 918559 A 2/1963
WO 2015020624 A1 2/2015

OTHER PUBLICATIONS

International Preliminary Examine Authority, Patent Cooperation Treaty, International Preliminary Report on Patentability, International Application No. PCT/US1353550, which is a parent PCT to the instant application, dated Aug. 14, 2015.
(Continued)

*Primary Examiner* — Patrick Assouad
*Assistant Examiner* — Haidong Zhang
(74) *Attorney, Agent, or Firm* — Howard L. Speight, PLLC

(57) ABSTRACT

An apparatus includes a helical flow tube in a formation testing tool. A current injector injects an electromagnetic current into the flow tube. A receiver coil is positioned to produce a receiver coil signal in response to the electromagnetic current. A processor is coupled to the receiver coil to calculate a conductivity of a fluid flowing through the flow tube based on the receiver coil signal.

10 Claims, 18 Drawing Sheets

(51) Int. Cl.
  *G01V 3/28* (2006.01)
  *G01N 33/28* (2006.01)
  *G01N 27/02* (2006.01)
  *G01N 27/08* (2006.01)
  *E21B 49/08* (2006.01)
(52) U.S. Cl.
  CPC ......... *G01N 27/08* (2013.01); *G01N 33/2823* (2013.01); *G01V 3/28* (2013.01); *E21B 2049/085* (2013.01)

(56) References Cited

U.S. PATENT DOCUMENTS

| | | | |
|---|---|---|---|
| 3,989,009 A | 11/1976 | Robar et al. | |
| 4,010,715 A | 3/1977 | Robar et al. | |
| 4,138,639 A | 2/1979 | Hutchins | |
| 4,912,415 A | 3/1990 | Sorensen | |
| 5,146,167 A * | 9/1992 | Strickland | G01V 3/28 |
| | | | 324/339 |
| 5,341,100 A | 8/1994 | Taylor | |
| 5,343,153 A | 8/1994 | Davies et al. | |
| 5,959,455 A | 9/1999 | Brown | |
| 7,414,406 B2 * | 8/2008 | Banning | G01V 3/30 |
| | | | 324/338 |
| 2003/0038634 A1 | 2/2003 | Strack | |
| 2005/0024060 A1 | 2/2005 | Bittar | |
| 2008/0238427 A1 * | 10/2008 | Clark | G01V 3/20 |
| | | | 324/347 |
| 2009/0167309 A1 * | 7/2009 | Homan | G01V 3/28 |
| | | | 324/339 |
| 2009/0266755 A1 * | 10/2009 | Fenton | E21B 43/385 |
| | | | 210/170.07 |
| 2010/0063738 A1 | 3/2010 | Roy et al. | |

OTHER PUBLICATIONS

International Searching Authority, Patent Cooperation Treaty, International Search Report and Written Opinion, International Application No. PCT/US2013/053550, which is a parent PCT to the instant application, dated Feb. 6, 2014.

Australian Government IP Australia, Patent Examination Report No. 1, Patent Application No. 2013397583, which is an AU counterpart to the instant application, dated Jun. 15, 2016.

European Patent Office, Communication pursuant to Rule 164(1) EPC, Application No./Patent No. 13891330.6-1554 / 2989490 PCT/US2013053550, which is an EP counterpart to the instant application, dated Dec. 12, 2016.

* cited by examiner

MEASURING FLUID CONDUCTIVITY

BACKGROUND

In hydrocarbon drilling operations, it may be useful to determine the resistivity or conductance of a downhole fluid. The resistivity and conductivity of such fluids can vary over a large range.

DETAILED DESCRIPTION

Figure 1:
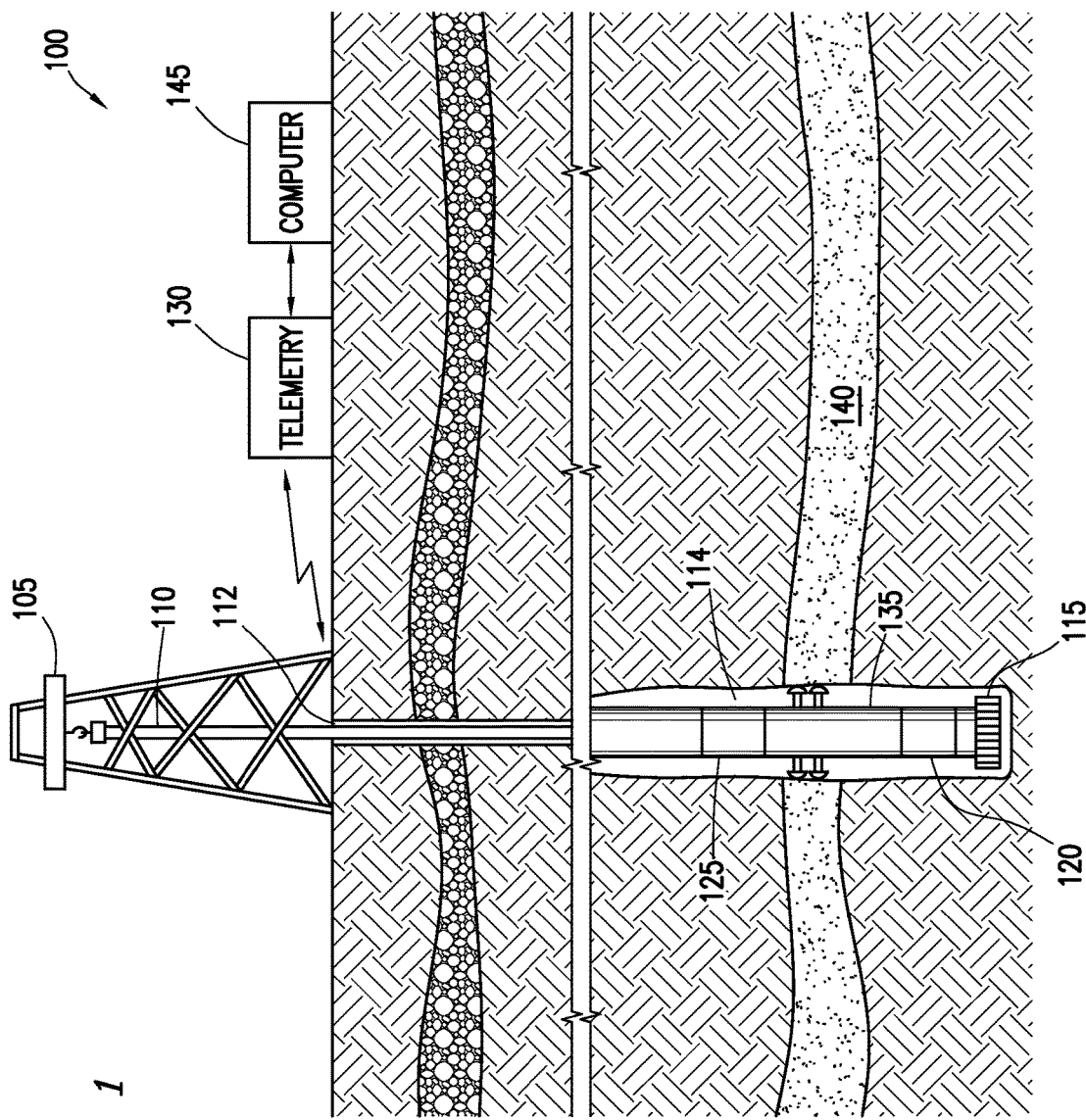
FIG. 1 shows a drilling system.

In one embodiment, a drilling system 100, illustrated in FIG. 1, includes a derrick 105 from which a drill string 110 is suspended in a borehole 112. FIG. 1 is greatly simplified and for clarity does not show many of the elements that are used in the drilling process. Further, while FIG. 1 shows a land-based drilling system, the equipment and techniques described herein are also useful in a sea-based drilling system and in wireline and slickline systems and operations. In one embodiment, the volume within the borehole 112 around the drill string 110 is called the annulus 114. In one embodiment, the drill string includes a bit 115, a variety of actuators and sensors, shown schematically (i.e., intended to show the main features or relationships but not the details) by element 120, and a telemetry section 125, through which the downhole equipment 120, 125, 135 communicates with a surface telemetry system 130. In one embodiment, the drill string 110 includes a formation testing tool 135 to collect data about fluid extracted from sub-surface formations, such as formation 140.

In one embodiment, a computer 145 receives data from the downhole equipment 120, 125, 135 and sends commands to the downhole equipment 120, 125, 135 through the surface telemetry system 130. In one embodiment the computer 145 includes input/output devices, memory, storage, and network communication equipment, including equipment necessary to connect to the Internet (not shown in FIG. 1).

Figure 2:
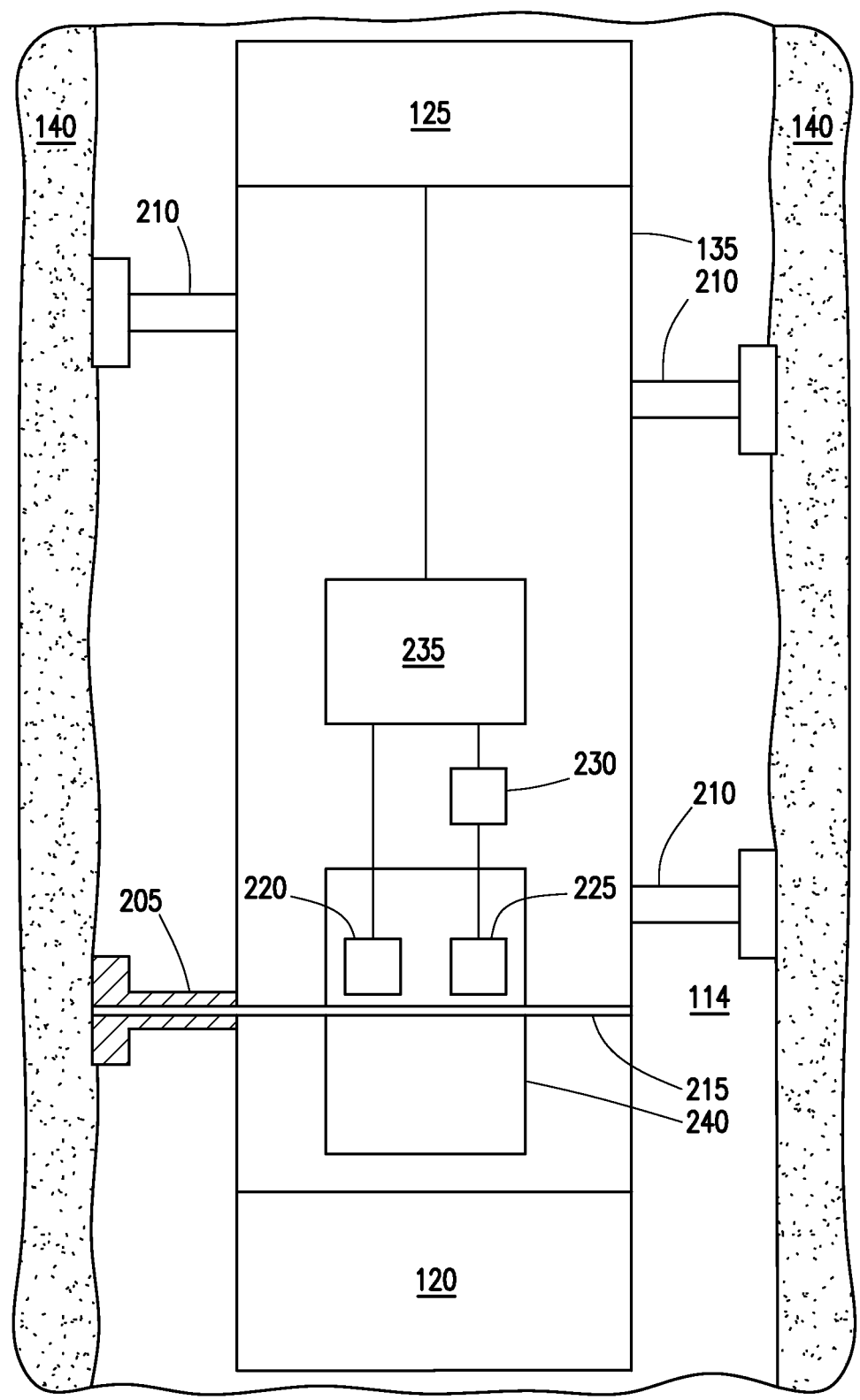
FIGS. 2 and 3 show schematic representations of a formation testing tool.

In one embodiment, illustrated schematically in FIG. 2, the formation testing tool 135 includes a probe 205 that retractably presses against the formation 140, allowing fluid to be extracted from the formation 140 with the use of valves, pumps, and other equipment not shown in FIG. 2. In one embodiment, the formation testing tool 135 includes one or more standoffs 210 to hold the formation testing tool 135 in position as fluid is extracted.

In one embodiment, the formation testing tool 135 includes a flow tube 215 through which fluid extracted from the formation 140 flows. In one embodiment, extracted fluid flows through the flow tube 215 and is released into the annulus 114 after being tested. In one embodiment (not shown), samples of the fluid are retained in containers in the formation testing tool 135 for further testing on the surface.

In one embodiment, the formation testing tool 135 includes a current injector 220 to inject a current into the fluid flowing through the flow tube 215. In one embodiment, the formation testing tool 135 includes a current receiver 225 to detect a current flowing in the fluid flowing through the flow tube 215 by, for example, detecting the electromagnetic field generated by the current.

In one embodiment, a measurement circuit 230 receives a signal from the current receiver 225 and produces an amplitude signal representing the amplitude of the signal from the current receiver 225 and a phase signal representing the phase of the signal from the current receiver. In one embodiment, the measurement circuit 230 provides the amplitude signal and the phase signal to a processor 235. In one embodiment, the amplitude and phase information are separated by the processor 235 rather than the measurement circuit 230. In one embodiment, the processor 235 processes the amplitude signal and the phase signal and calculates a conductivity of the formation fluid flowing through the flow tube 215, as described in more detail below.

In one embodiment, some or all of the formation testing tool 135 components 215, 220, 225, 230, and 235 are enclosed in a housing 240.

Figure 3:
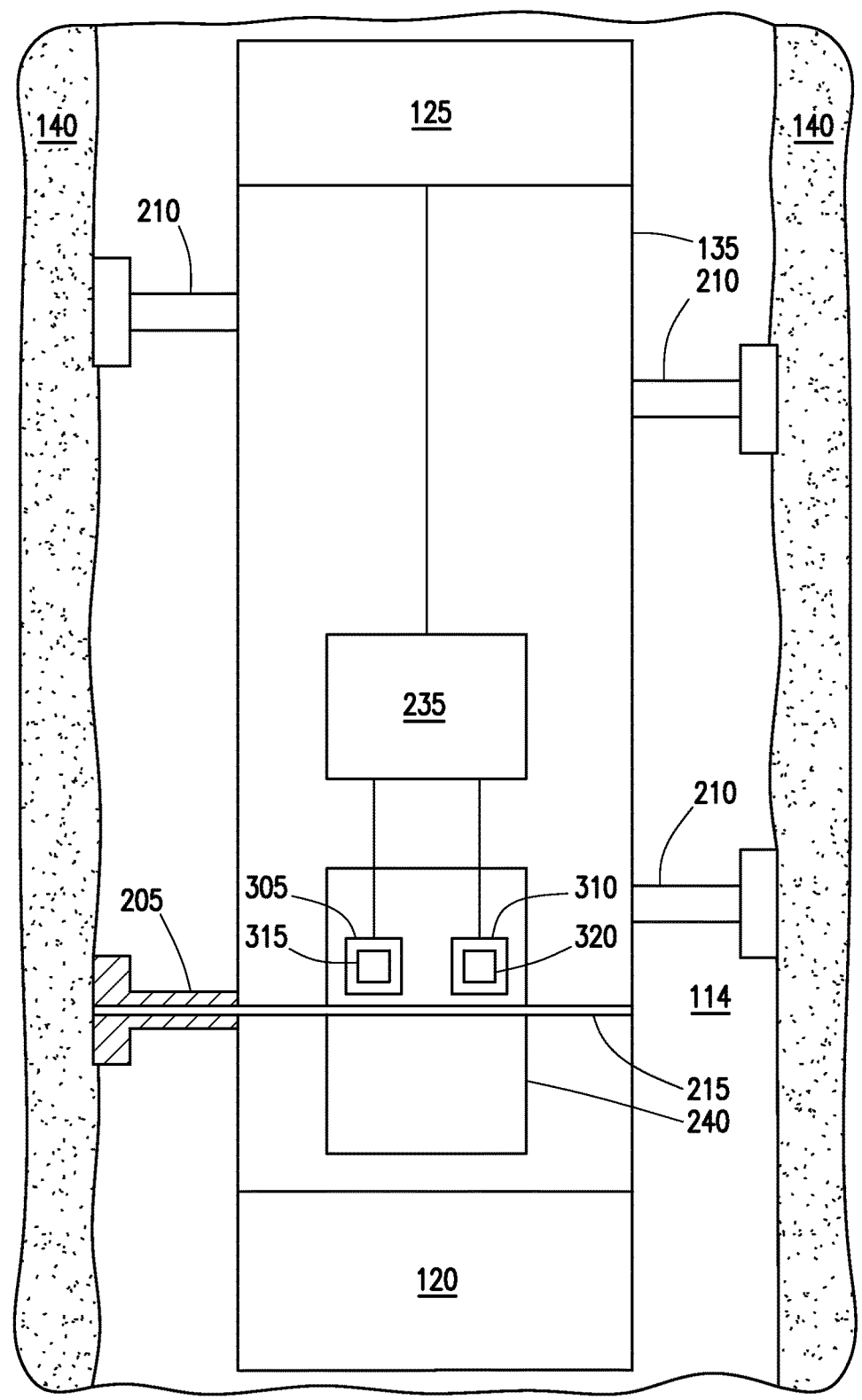

In one embodiment, illustrated in FIG. 3, in which the components identified by reference numbers 205 (probe), 210 (standoff), 215 (flow tube), 235 (processor), and 240 (housing) are as described above with respect to FIG. 2, the formation testing tool 135 includes a resistance measurement device 305 to measure the resistance of the fluid flowing through the flow tube 215 and a conductance measurement device 310 to measure the conductance of the fluid flowing through the flow tube 215 (where conductance=1/resistance).

In one embodiment, the resistance measurement device 305 includes an analog to digital converter (A/D) 315 that converts an analog signal representing the resistance of the fluid flowing through the flow tube 215 to a digital representation that is provided to the processor 235. Similarly, in one embodiment, the conductance measurement device 305 includes an analog to digital converter (A/D) 320 that converts an analog signal representing the conductance of the fluid flowing through the flow tube 215 to a digital representation that is provided to the processor 235.

The A/D converters 315 and 320 are subject to resolution limitations that are common to such devices. In particular, the resolution of the A/D converters 315 and 320 diminishes for small signals. In one embodiment, the resistance measurement device 305 produces a more useful output (e.g., an output with greater resolution) than the conductance measurement device 310 when the resistance of the fluid flowing through the flow tube 215 is high. Similarly, in one embodiment, the conductance measurement device 310 produces a more useful output (e.g., an output with greater resolution) than the resistance measurement device 305 when the conductance of the fluid flowing through the flow tube 215 is high.

In one embodiment, the processor 235 accepts inputs from the resistance measurement device 305 and the conductance measurement device 310 and reports the measurement with the greatest magnitude to the computer 145. In that way, the processor reports the most useful and highest resolution measurement for the fluid being evaluated. In one embodiment, the processor 235 reports the resistance measurement and the conductance measurement to the computer 145.

In one embodiment, the conductance measurement device 310 includes the current injector 220, current receiver 225, and measurement circuit 230 shown in FIG. 2.

Figure 4:
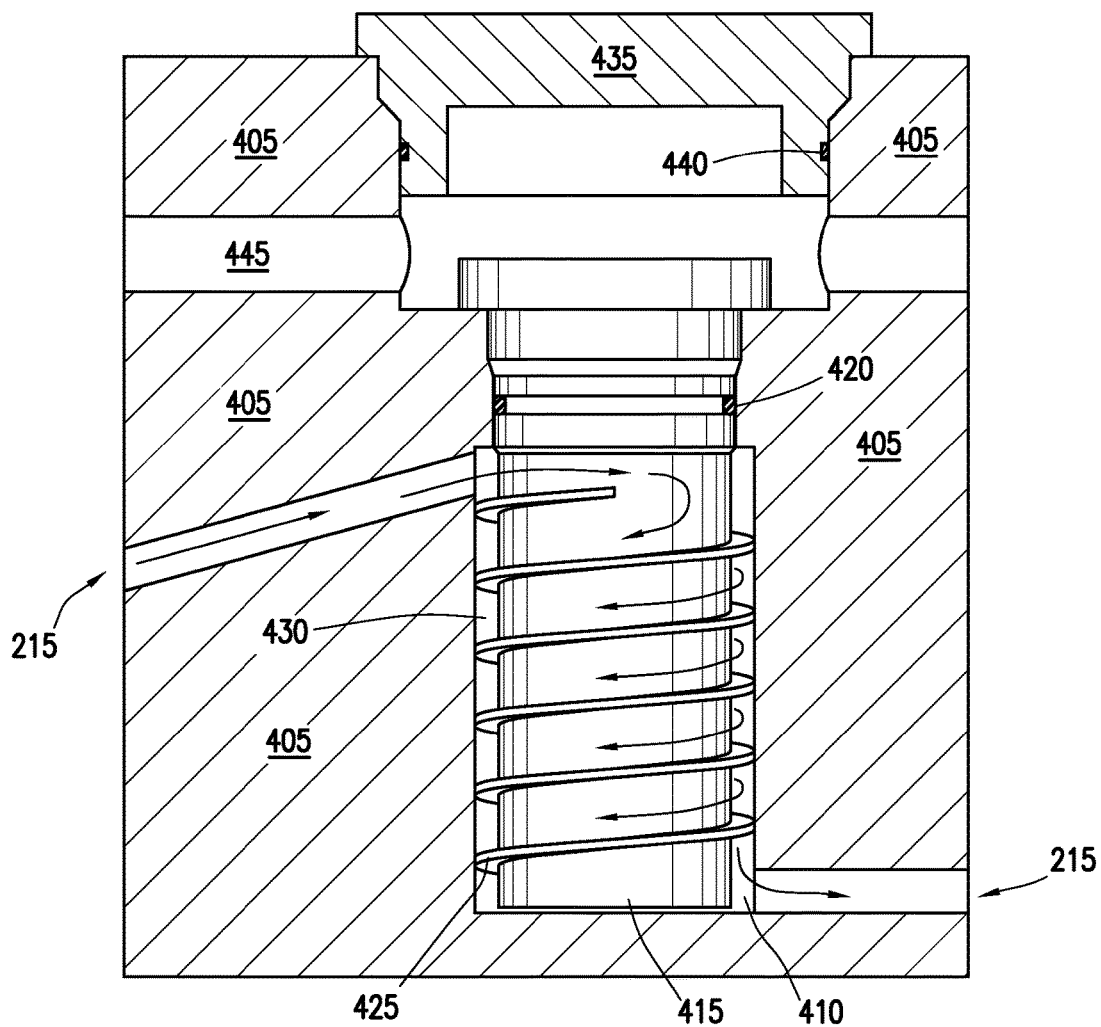
FIG. 4 shows a flow tube.

In one embodiment, shown in FIG. 4, the flow tube 215 is formed in a body 405 of the formation testing tool 135. In one embodiment, a finned housing 415 is placed into a chamber 410 formed in the housing 405 and is held in place by threads (not shown) in the body 405 or by another suitable technique. In one embodiment, the finned housing 415 is made of a ceramic material. In one embodiment, the finned housing 415 is made of polyether ether ketone ("PEEK"). In one embodiment, an o-ring 420 seals the chamber 410.

In one embodiment, the finned housing 415 includes a helical fin 425 that spirals around the finned housing 415 and presses against an inner surface of the chamber 410 forming a helical tube 430 that spirals around the finned housing 415. In one embodiment, the helical fin 425 spirals around the finned housing 415 in the opposite direction from that shown in FIG. 4, such that, when seen in the view of FIG. 4, each segment of the helical fin 425 appears to drop (rather than rise as it does in FIG. 4) from the left to the right of the finned housing 415. In one embodiment, the flow tube 215 enters the helical tube 430 at the upper left of the chamber 410, as shown in FIG. 4. In one embodiment, the helical tube 430 exits into the flow tube 215 at the lower right of the chamber 410, as shown in FIG. 4. In one embodiment, fluids flow through the flow tube 215 and the helical tube 430 as indicated by the arrows in FIG. 4. In one embodiment, fluids flow in the direction opposite to that shown in FIG. 4. In one embodiment, the helical tube 430 is part of the flow tube 215.

In one embodiment, a cap 435, sealed by an o-ring 440, allows access to the finned housing 415. A conduit 445, for routing wires, optical fibers, etc., is formed in the body 405.

Figure 5:
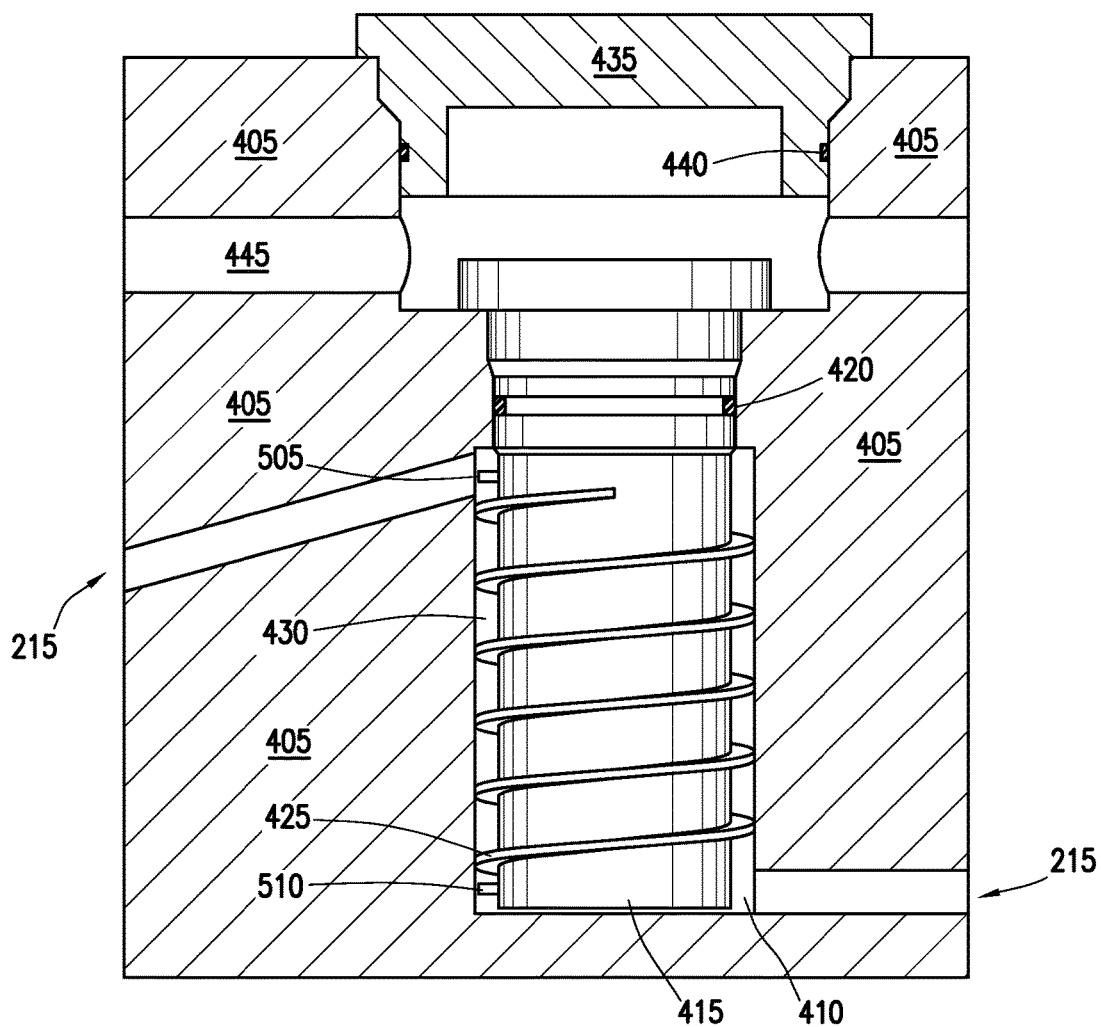
FIG. 5 shows electrodes being used as a current injector.

In one embodiment, illustrated in FIG. 5, the current injector 220 includes a first electrode 505 at one end of the helical tube 430 and a second electrode 510 at the other end of the helical tube 430.

In one embodiment, an alternating current ("AC") voltage is applied across the first electrode 505 and the second electrode 510, which causes a time-varying current to flow through any fluid flowing through the helical tube 430 portion of the flow tube 215, which in turn creates a time-varying electromagnetic field. In one embodiment, in the configurations shown in FIGS. 4-7, the body 405 is made of an insulating material, such as PEEK. In one embodiment, the flow tube 215, including the helical tube 430 portion of the flow tube 215, is coated with an insulating material, such as PEEK, to prevent the current injected by the electrodes 505 and 510 from passing through the body 405 instead of traversing the length of the helical tube 430 portion of the flow tube 215.

Figure 6:
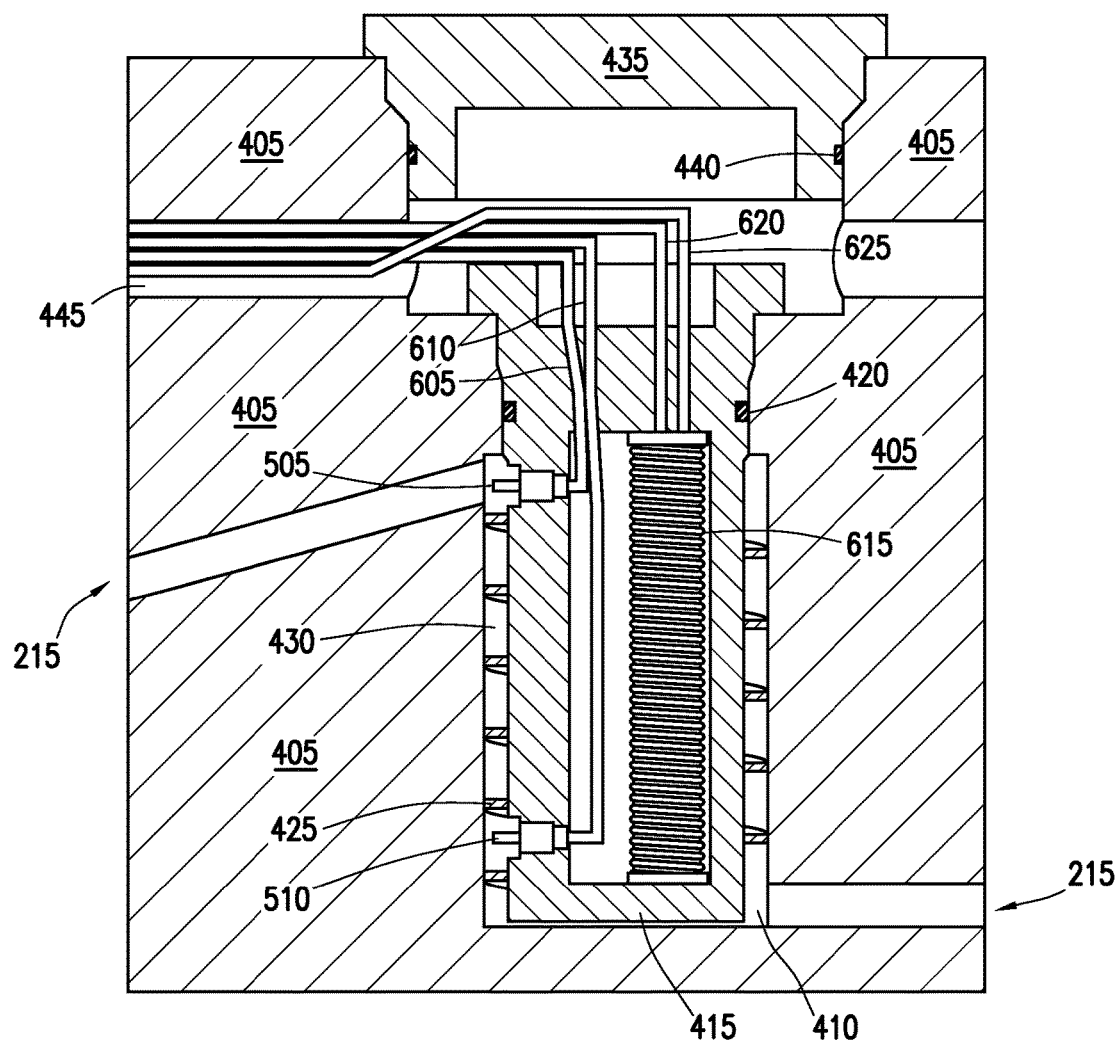
FIGS. 6, 8, and 9 show conductance measurement devices.

In one embodiment, illustrated in FIG. 6, the first electrode 505 is coupled to a first electrode lead 605, which, in one embodiment, couples the first electrode 505 to the processor 235. In one embodiment, the second electrode 510 is coupled to a second electrode lead 610, which, in one embodiment, couples the second electrode 610 to the processor 235.

In one embodiment, the current receiver 225 includes a coil 615 embedded in the finned housing 415. Leads 620 and 625, which are coupled to the ends of coil 615, couple any current induced in the coil 615 to the measurement circuit 230. In one embodiment, the time-varying electromagnetic field induced by the current flowing through the fluid flowing through the helical tube 430 (generated by the time-varying voltage across the first electrode 505 and the second electrode 510) induces a current in the coil 615 which is related to properties of the fluid, as described in more detail below. In one embodiment, because of its sensitivity to small currents, the device shown in FIG. 6 is a conductance measurement device.

Figure 7:
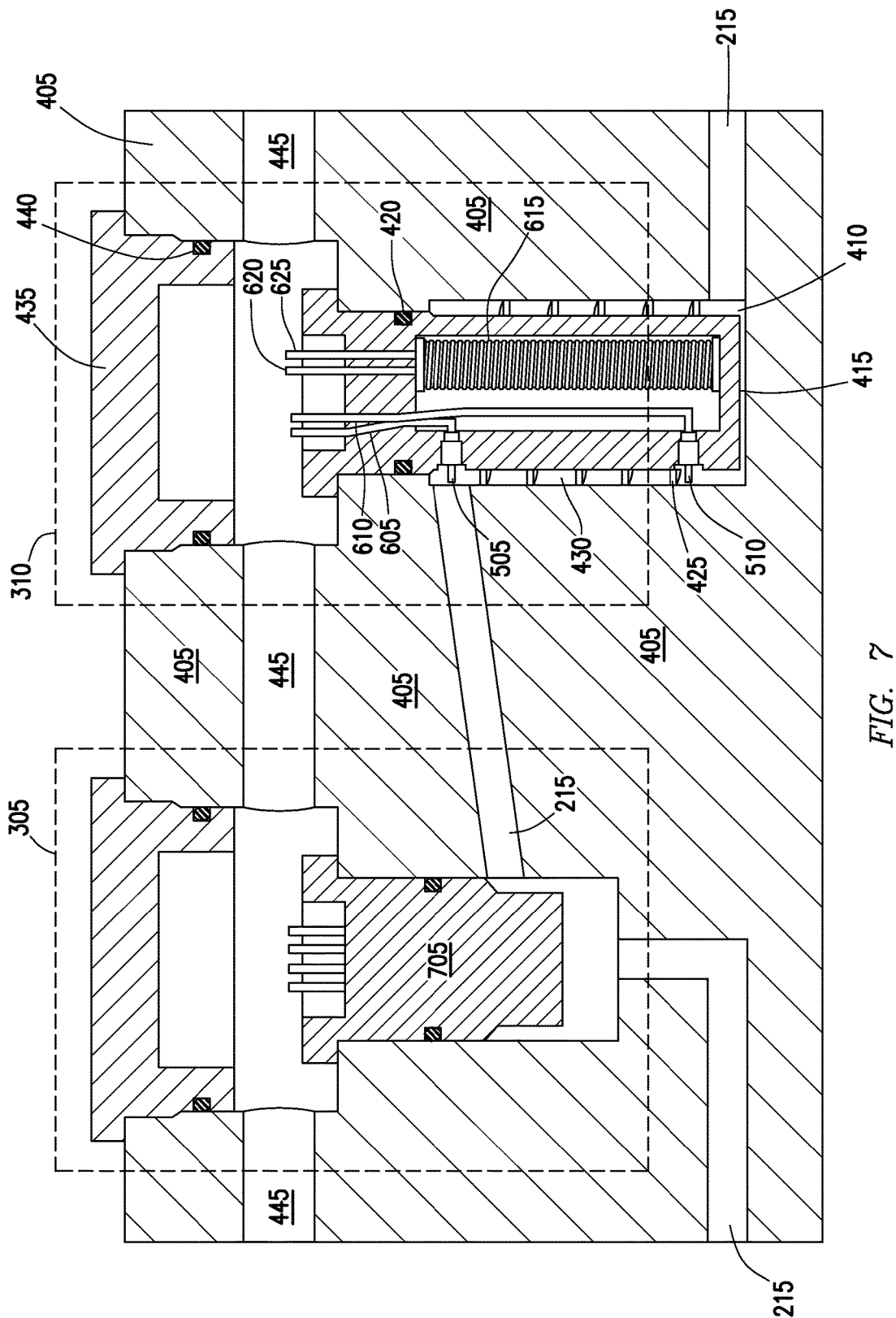
FIG. 7 shows a resistance measurement device and a conductance measurement device.

In one embodiment, illustrated in FIG. 7, the conductance measurement device 310 is coupled to the resistance measurement device 305 by the flow tube 215 and the conduit 445. In one embodiment, the conductance measurement device 310 includes the components illustrated in FIG. 6. In one embodiment, the resistance measurement device 305 includes a resistivity button 705, described in more detail with respect to FIGS. 18 and 19 below.

Figure 8:
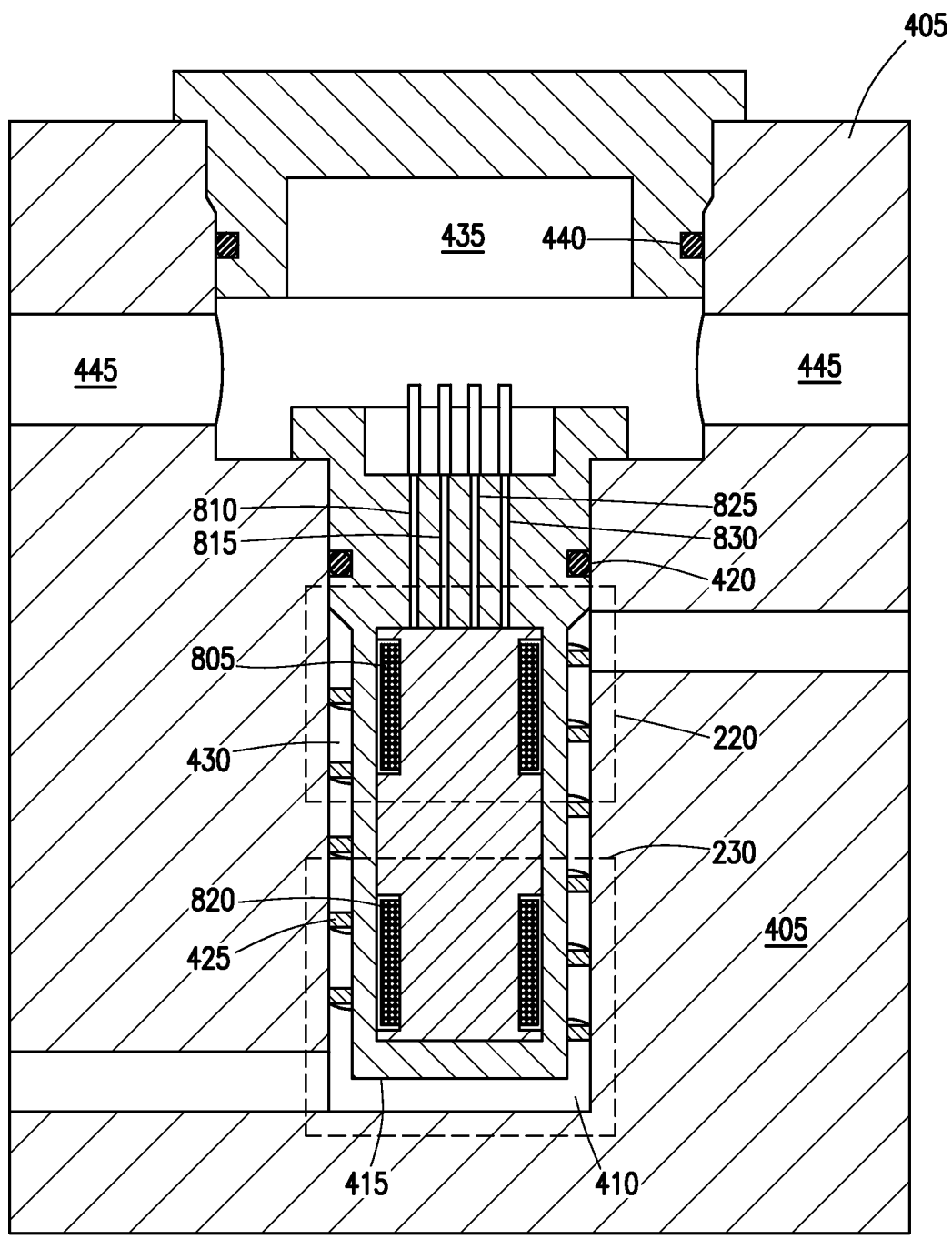

In one embodiment, illustrated in FIG. 8, the current injector 220 includes a coil 805 that is coupled to the processor 235 by leads 810 and 815. In one embodiment, the current receiver 225 includes a coil 820 that is coupled to the measurement circuit 230 by leads 825 and 830. In one embodiment, the coil 805 induces a time-varying current in the helical tube 430 portion of the flow tube 215, which in turn induces a time-varying magnetic field. In one embodiment, the time-varying magnetic field induces a current in the coil 820 which is coupled to the measurement circuit 230 by leads 825 and 830.

In one embodiment, coil 805 is coaxial with coil 820. In one embodiment, coil 805 is identical to coil 810.

In one embodiment, the roles of the coils 805 and 820 are reversed. That is, in one embodiment, coil 805 is included in the current receiver 225 and is coupled to the measurement circuit 230 and the coil 820 is included in the current injector 220 and is coupled to the processor 230.

Figure 9:
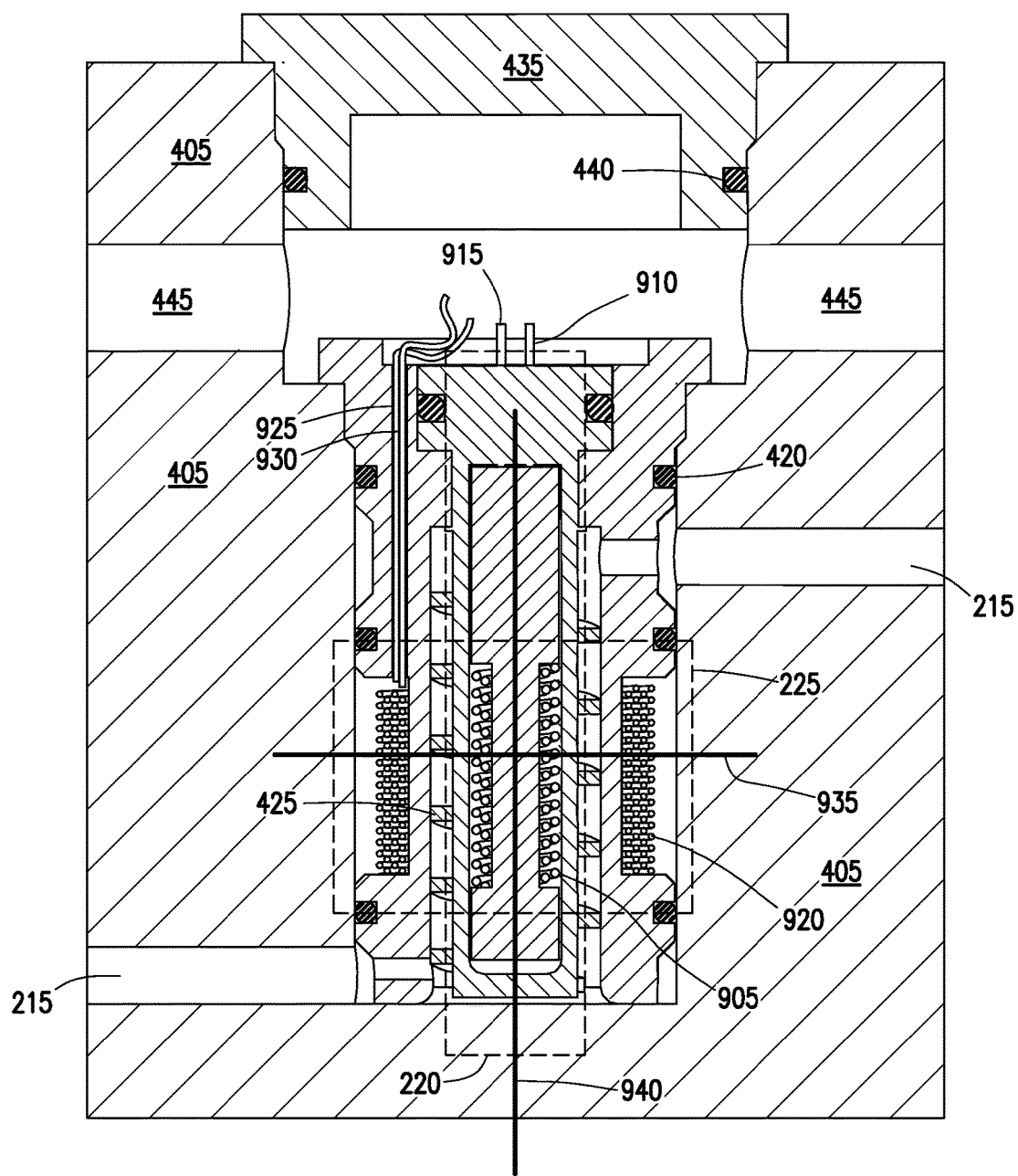

In one embodiment, illustrated in FIG. 9, the current injector 220 includes a coil 905 that is coupled to the processor 235 by leads 910 and 915. In one embodiment, the current receiver 225 includes a coil 920 that is coupled to the measurement circuit 230 by leads 925 and 930. In one embodiment, the coil 905 induces a time-varying current in the helical tube 430 portion of the flow tube 215, which in turn induces a time-varying magnetic field. In one embodiment, the time-varying magnetic field induces a current in the coil 920 which is coupled to the measurement circuit 230 by leads 925 and 930.

In one embodiment, coil 905 is coaxial with coil 920. In one embodiment, coil 905 is positioned relative to coil 920 such that a line 935, perpendicular to an axis 940 coincident with the axes of coils 905 and 920, which passes through coil 905 also passes through coil 920. In one embodiment, coil 905 is aligned with coil 920 such that line 935 passes through the center of coil 905 and through the center of coil 920.

In one embodiment, the roles of the coils 905 and 920 are reversed. That is, in one embodiment, coil 905 is included in the current receiver 225 and is coupled to the measurement circuit 230 and the coil 920 is included in the current injector 220 and is coupled to the processor 230.

In one embodiment, in the configurations illustrated in FIGS. 8 and 9, the body 405 is made of an insulating material, such as PEEK, or the flow tube, including the helical tube 430 portion of the flow tube 215, is coated with an insulating material, such as PEEK, as discussed above in connection with FIGS. 4-7. In one embodiment, in the configurations illustrated in FIGS. 8 and 9, the body is made of metal, such as steel, or another suitable material.

Figure 10:
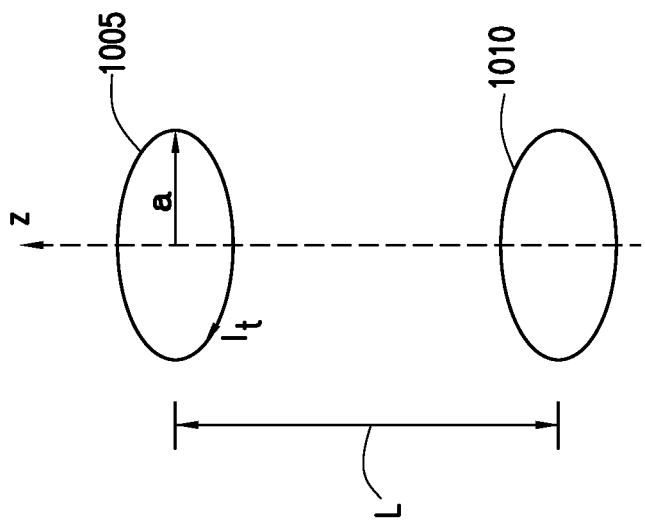
FIG. 10 shows a simplified model of an induction logging system.

In one embodiment, the formation testing tools illustrated in FIGS. 2-9 use an induction logging technique to measure the conductivity of the fluid flowing through the flow tube 215. Induction logging is based on measuring the induced voltage at a receiver due to a known transmitter current. The system in FIG. 10 is one embodiment of a simplified model of an induction logging system consisting of a transmitter coil 1005 and a receiver coil 1010 separated by a distance of L in an otherwise homogeneous medium (e.g., a formation) of conductivity σ. In one embodiment, the radius of the transmitter coil 1005 and the receiver coil 1010 is same and equal to a. The system illustrated in FIG. 10 is similar to the two-coil systems shown in FIGS. 8 and 9 and is analogous to the electrode and coil system illustrated in FIGS. 5, 6, and 7, in which the transmitter current is generated by electrodes rather than a coil.

In one embodiment, a time harmonic current of amplitude $I_t$ and angular frequency ω is generated in the transmitter. Assuming transmitter coil has $N_T$ turns and receiver coil has $N_R$ turns, the voltage received at the receiver is equal to:

$$V = \frac{2N_T N_R I_T (\pi a^2)^2}{4\pi} \frac{(i\omega\mu)}{L^3}(1 - ikL)e^{ikL} \quad (1)$$

where:
$k^2 = i\omega\mu\sigma$,
μ is the permeability of the formation,
σ is the conductivity of the formation, and
L is the distance between the transmitter coil 1005 and the receiver coil 1010.
V can be expanded in a power series to obtain:

$$V = K\left[\sigma + \frac{2i}{\omega\mu L^2} - \frac{2}{3}\left(\frac{L}{\delta}\right)\sigma(1+i) + ...\right] \quad (2)$$

where:

$$\delta = \sqrt{\frac{2}{\omega\mu\sigma}} \text{ is the skin depth} \quad (3)$$

and $$K = \frac{N_T N_R I_T (\pi a^2)^2 \omega^2 \mu^2}{4\pi L}.$$

As can be seen, in a simple homogeneous medium, the real part of the voltage V is approximately proportional to the formation conductivity (σ), with the proportionality constant being a "tool constant" (K). It should be noted that the imaginary part of the voltage is mainly due to the direct fields and it is stronger than the real part for low frequencies. Consequently, in one embodiment, the imaginary part of the voltage is eliminated using bucking receivers as in traditional well logging induction tools.

Figure 11:
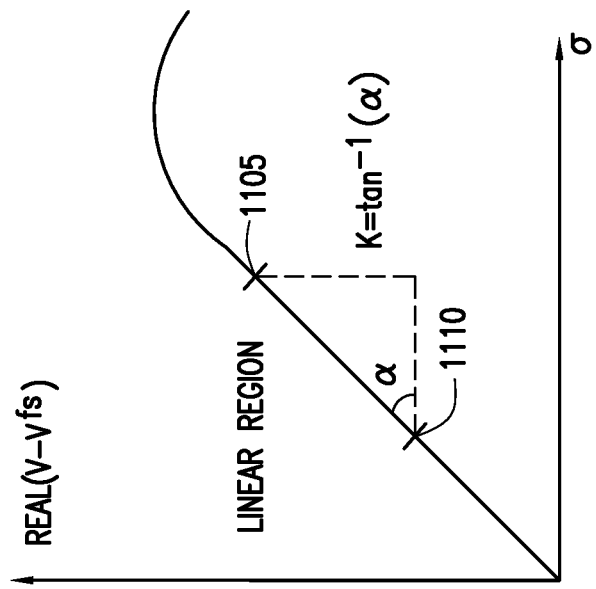
FIG. 11 is a chart showing the relationship between the real part of a measured signal and conductivity.

In more realistic scenarios, the tool constant cannot be simply expressed as in equation (3) due to, for example, electromagnetic effects of presence of nearby objects. As a result, in one embodiment, a calibration procedure is used. In one embodiment, the calibration procedure is be done by placing the sensor in a fluid with varying conductivity and recording the changes in the measured signal V as shown in FIG. 11. Although the response shown in FIG. 11 is nonlinear, it can be approximated with a line over a large part of the operating region, e.g., from point 1105 to point 1110. The slope of this line is the desired proportionality constant:

$$K = \frac{Re(V - V^{fs})}{\sigma} \quad (4)$$

FIGS. 12-15 illustrate simulated responses of the system shown in FIG. 10 at different frequencies (FIG. 12 at 10 MHz, FIG. 13 at 10 MHz, FIG. 14 at 100 MHz, and FIG. 15 at 1 GHz), with a coil diameter (a) of 0.5 inches and a spacing (L) of 0.5 inches. The coils were simulated to be contained in an insulator having a diameter of 0.6 inches and to be placed in a pipe having a diameter of 1 inch.

FIGS. 12-15 show apparent conductivity as a function of fluid conductivity, where, in one embodiment, apparent conductivity is calculated as the signal measurement in the complex domain multiplied by a real valued tool constant after a tool body signal is subtracted out. In one embodiment, the tool constant and the tool body signal are measured for a given device by performing a calibration procedure where measurements are made with a known fluid.

Figure 12:
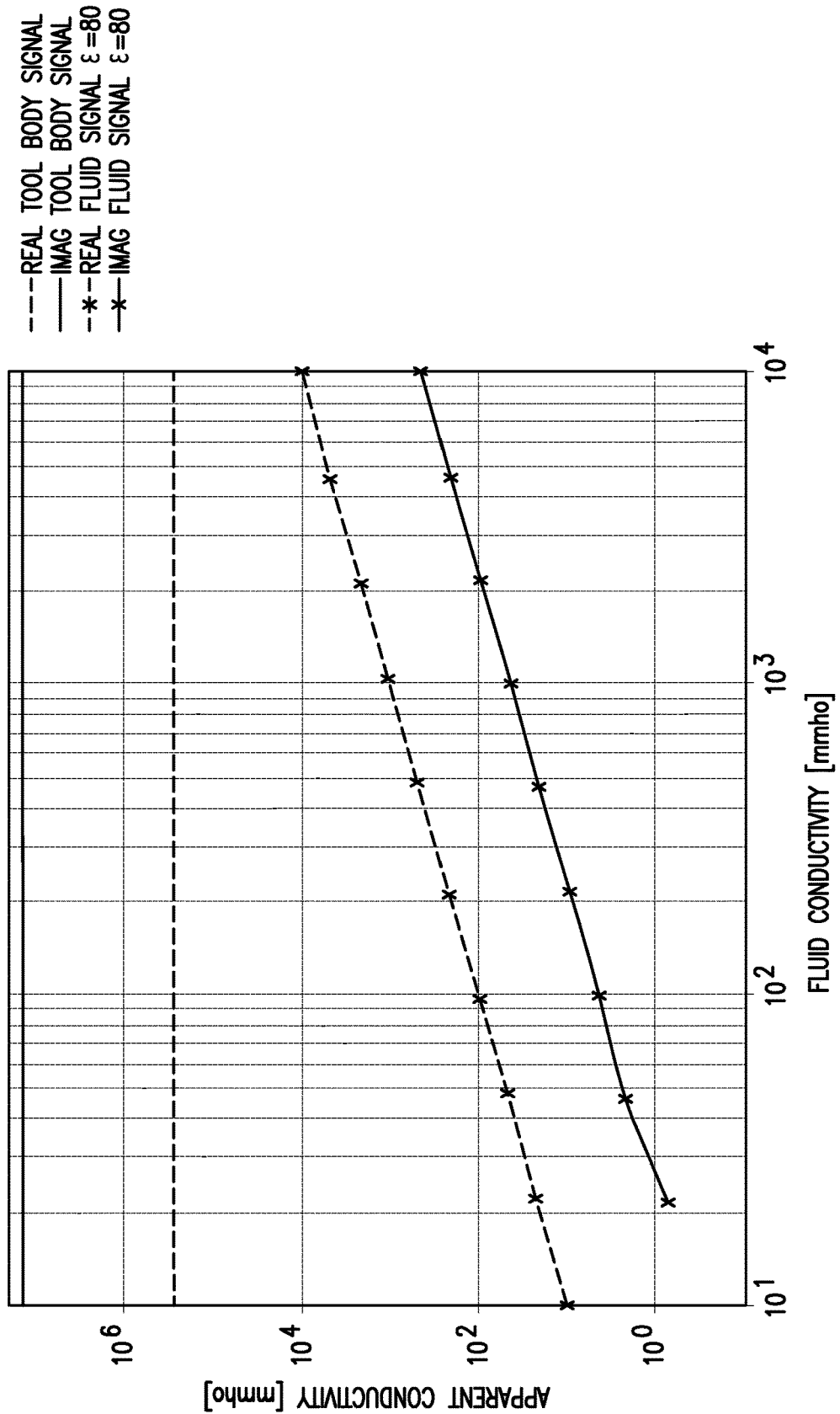
FIGS. 12-15 are charts showing apparent conductivity as a function of fluid conductivity.
Figure 13:
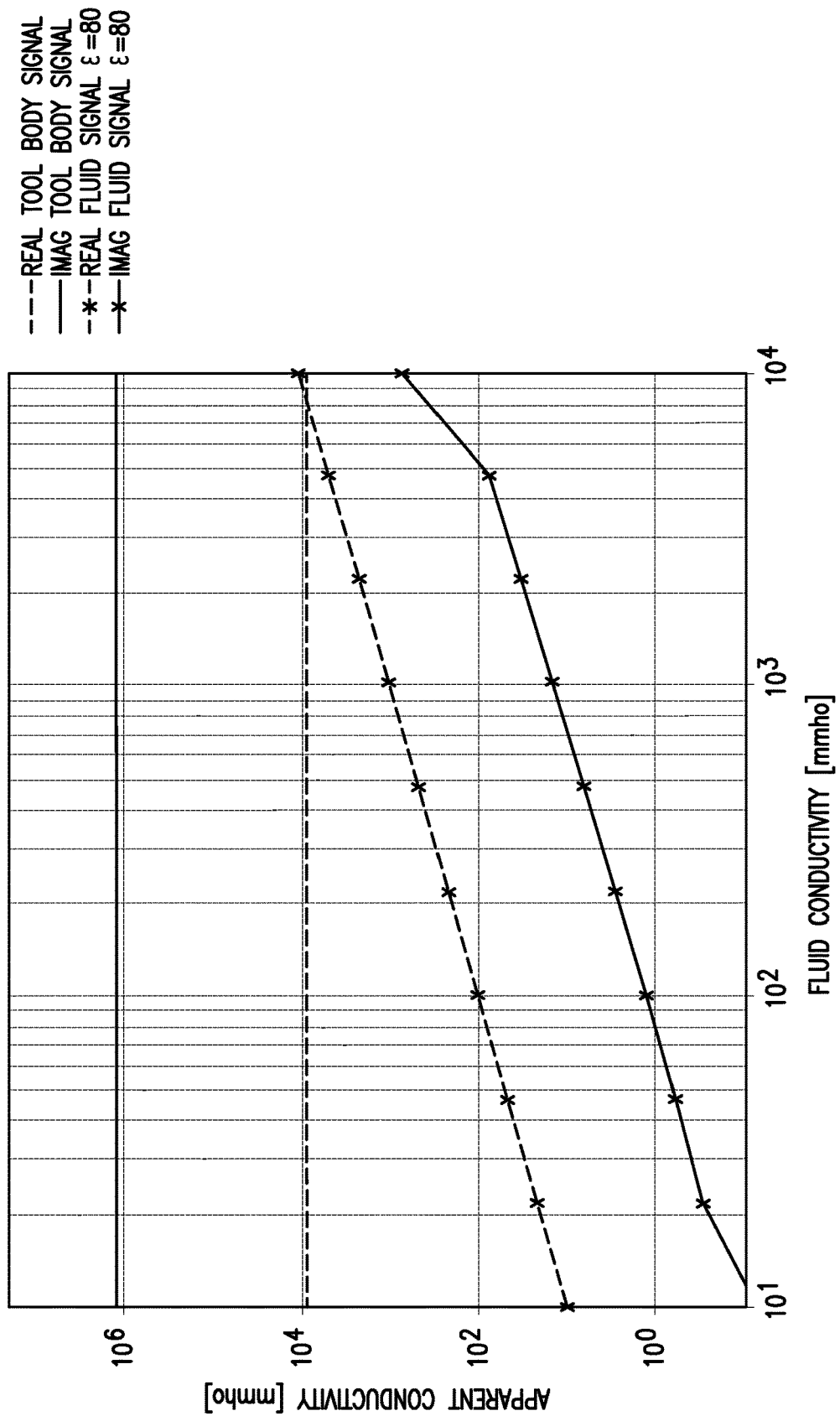
Figure 14:
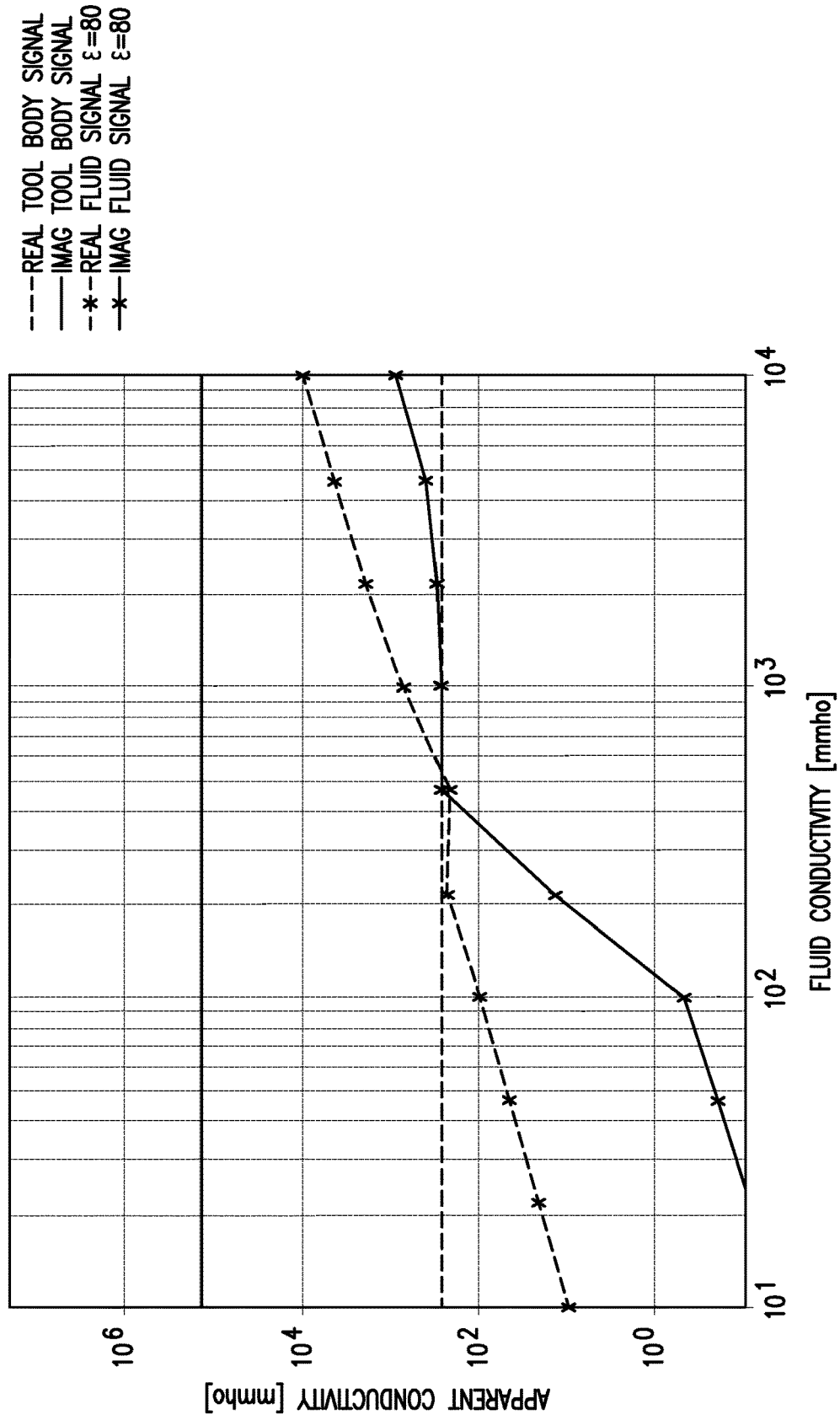
Figure 15:
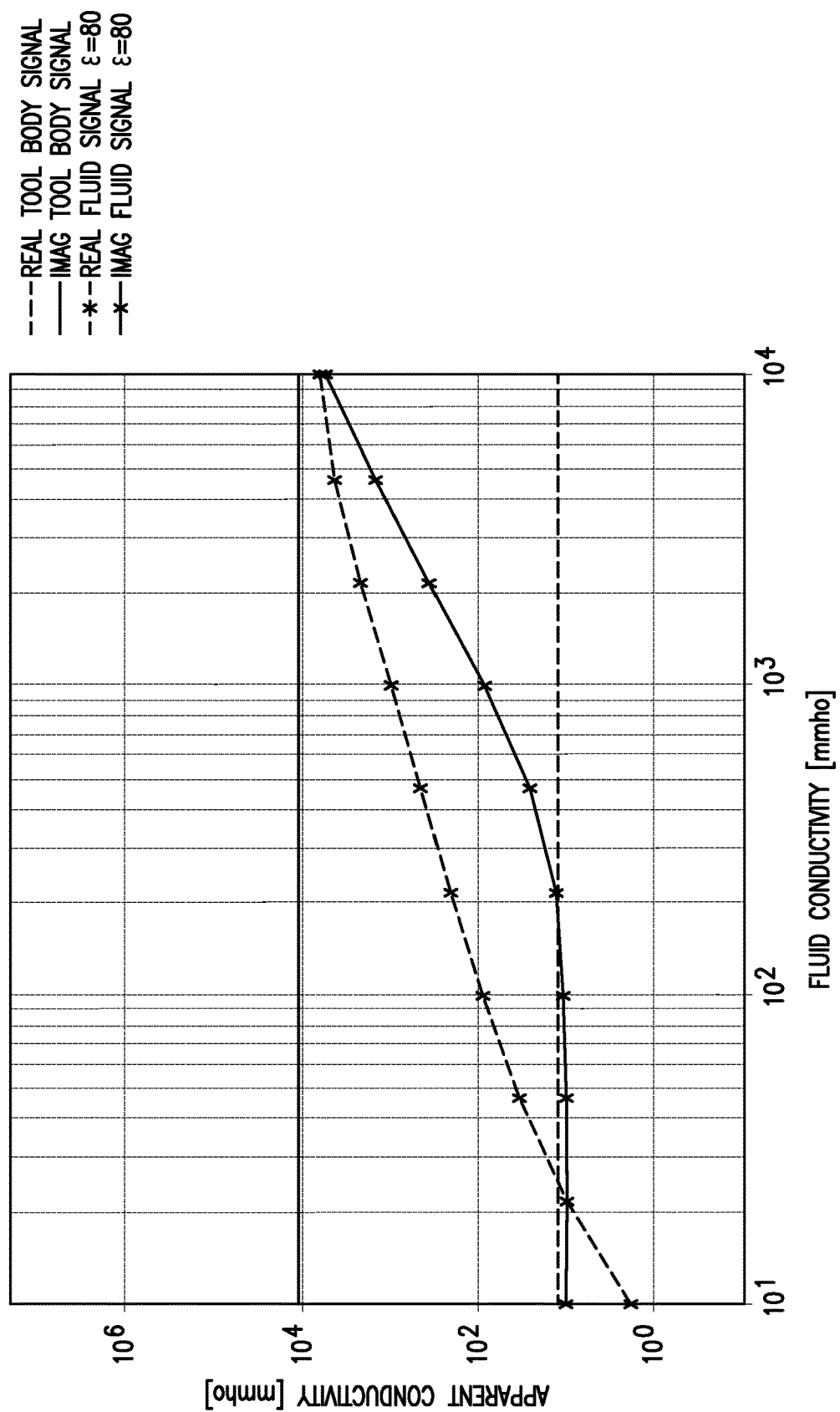

As can be seen in FIGS. 12-14, at relatively low frequencies, the tool body signal is much larger than the fluid signal, which requires a large dynamic range in measurement. At about 1 GHz, as seen in FIG. 15, the ratio of tool body signal to fluid signal is lower than about 60 dB for a wide range of fluid conductivity, and as a result an acceptable sensitivity is obtained. The effect of permittivity was observed to be very low, which indicates that it will have less influence on the measurement when compared to resistivity. In one embodiment, the current injector 220 and current receiver 225 operate in the 1 GHz range or higher.

Figure 16:
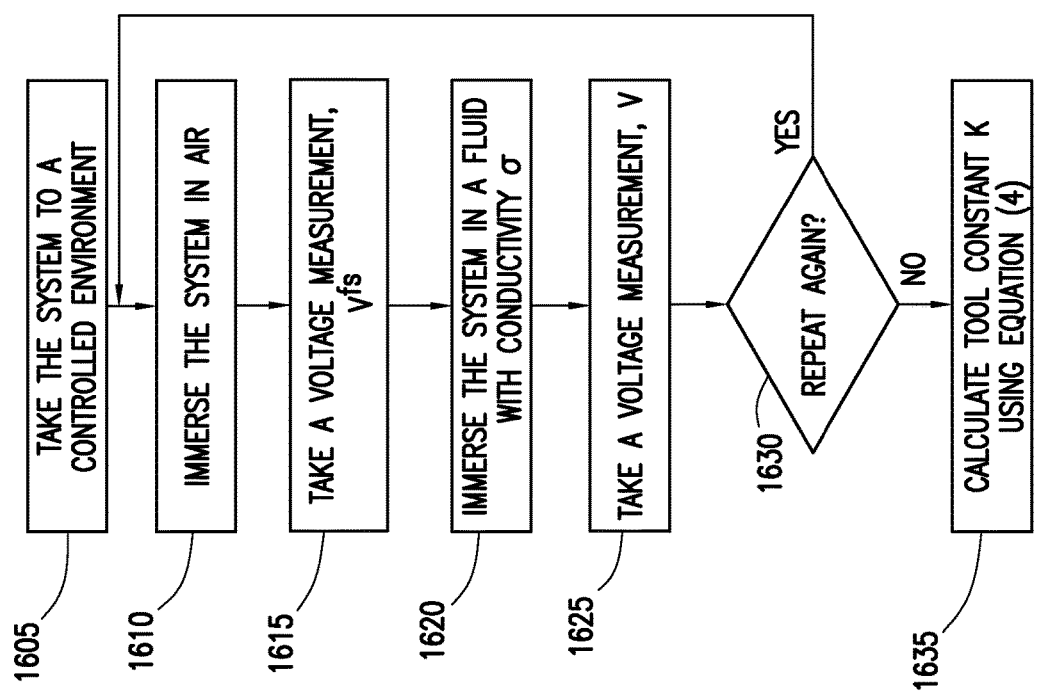

In one embodiment, as shown in FIG. 16, the system is calibrated to measure the proportionality constant K. In one embodiment, the system, such as the formation testing tool 135, is taken to a controlled environment, such as a laboratory (block 1605). The formation testing tool 135 is immersed in a known fluid, such as air (block 1610). In particular, the flow tube 215 is filled with the known fluid. A free-space voltage measurement, $V^{fs}$, is then taken (block 1615). This is accomplished by the current injector 220, under the control of the processor 235, injecting a time-varying current into the flow tube 215 to produce a time-varying electromagnetic field, which is detected by the current receiver 225 and measurement circuit 230 (which includes a bucking receiver to eliminate the imaginary part of the received signal) producing $V^{fs}$. That result is provided to the processor 235.

Continuing the calibration, in one embodiment the formation testing tool 135 is immersed in a fluid with a known conductivity σ (block 1620). In particular, in one embodiment, the flow tube 215 is filled with the known fluid with the known conductivity σ. A voltage measurement, V, is then taken (block 1625). Blocks 1610-1625 (or a subset of those blocks, e.g., blocks 1610-1615 or 1620-1625) are then optionally repeated (block 1630) a desired number of time to improve the accuracy of the result.

In one embodiment, the tool constant K is then calculated using equation (4) (block 1635), completing calibration.

Figure 17:
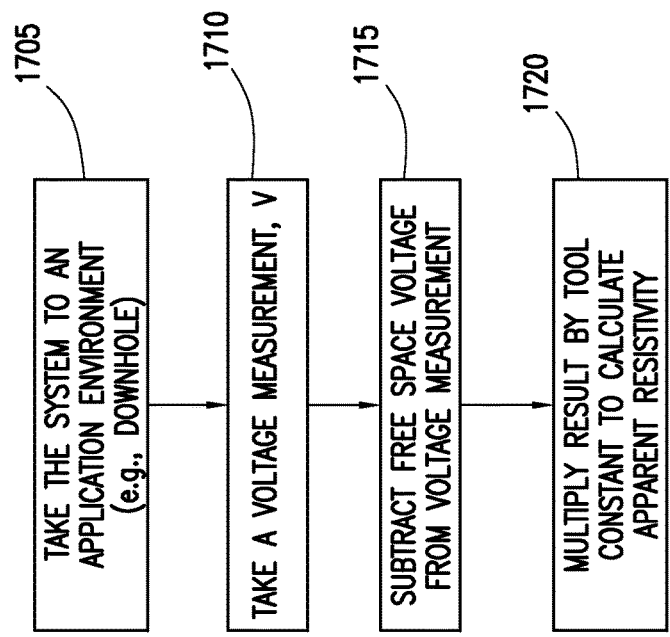
FIGS. 16, 17, and 20 are flow charts.

In one embodiment of use, as shown in FIG. 17, the formation testing tool 135 is taken to an application environment (block 1705), such as downhole as shown in FIG. 1. In one embodiment, a voltage measurement, V, is taken (block 1710). In one embodiment, the free-space voltage, $V^{fs}$, is subtracted from V (block 1715). The result is multiplied by the tool constant K to calculate apparent resistivity.

In one embodiment, the measured apparent resistivity of the fluid is used to make decisions regarding a well. For example, during a formation pump out test operation of a water bearing zone with water-based drilling fluid (mud), formation fluid contaminated with drilling mud is pumped through a port attached to the well bore. Since the resistivity of the drilling mud and that of the formation fluid are different, continuously monitoring the apparent resistivity of the fluid being pumped will give a clear indication as to the cleanness of the fluid, based on which a decision can be made to take formation samples with minimal contamination level.

Figure 19:
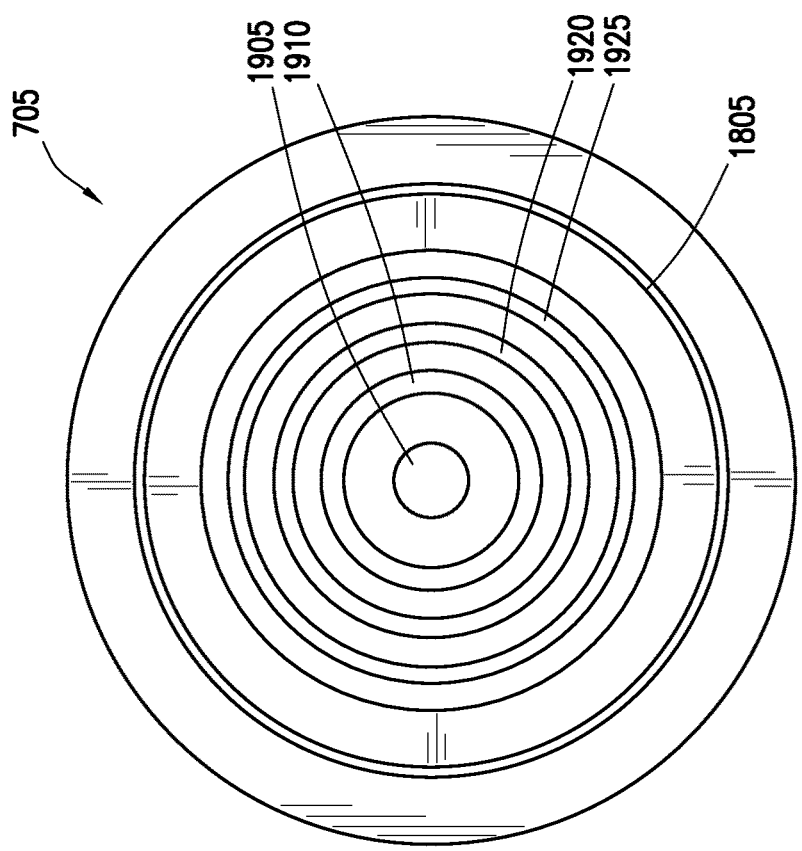
FIGS. 18 and 19 are views of a resistivity button.
Figure 18:
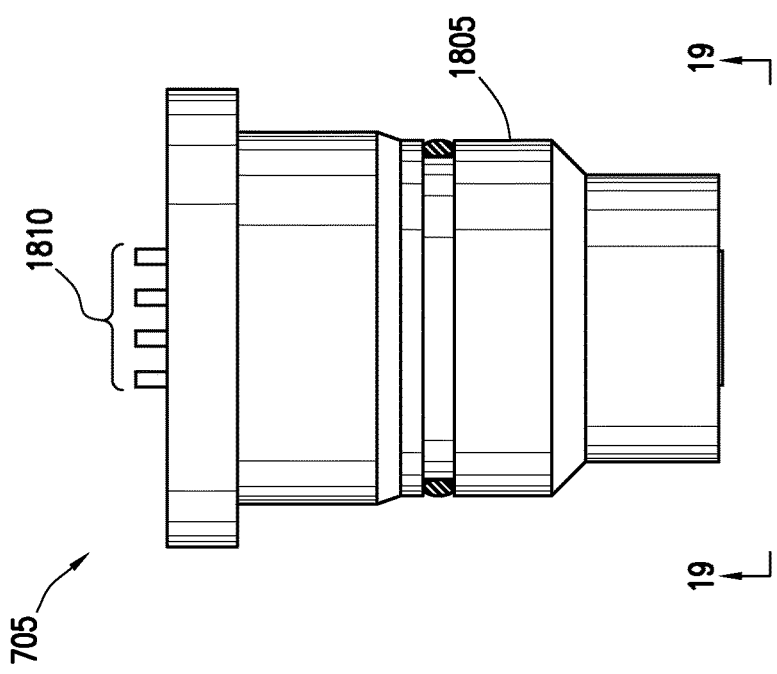

In one embodiment, illustrated in FIGS. 18 and 19, the resistivity button 705 includes a housing 1805 which allows it to be mounted in the formation testing tool 135 and leads 1810 that allow it to be connected to the processor 235. In one embodiment, the resistivity button 705 includes four electrodes: a center electrode 1905 and three concentric ring electrodes 1910, 1920, 1925. In one embodiment, the processor 235 causes a voltage V to be asserted across two of the electrodes, e.g., ring electrodes 1910 and 1920, and a current I is then measured flowing through the fluid flowing through the flow tube 215 from center electrode 1905 to ring electrode 1925. The resistance of the fluid is then calculated as:

$$R = \frac{V}{I} \quad (4)$$

In one embodiment, the resistivity, ρ, of the fluid is calculated by multiplying the resistance R, by a geometric factor G, i.e.

$$\rho = RG \quad (5)$$

In one embodiment, G depends on the position and geometry of the electrodes and the surrounding housing. In one embodiment, G is determined through calibration at the surface by injecting a fluid with known resistivity, measuring the resistance of the fluid, then using the relationship G=ρ/R. In one embodiment, G is determined as a function of environmental conditions such as temperature, and is applied based on the downhole conditions that the sensor is experiencing. This allows the sensor to preserve accurate calibration in a wide range of conditions.

In one embodiment, the electrodes 505 and 510 shown in FIGS. 5-7 are used to measure resistivity using these concepts. In one embodiment, such an approach includes:
1. measuring the voltage across electrodes 505 and 510 and the current flowing through electrodes 505 and 510 and through the fluid flowing through the helical tube 430 portion of the flow tube 215,
2. compute R using equation (4),
3. compute the resistivity, p, of the fluid flowing through the helical tube 430 portion of the flow tube 215 using equation (5) using G determined during calibration.

Figure 20:
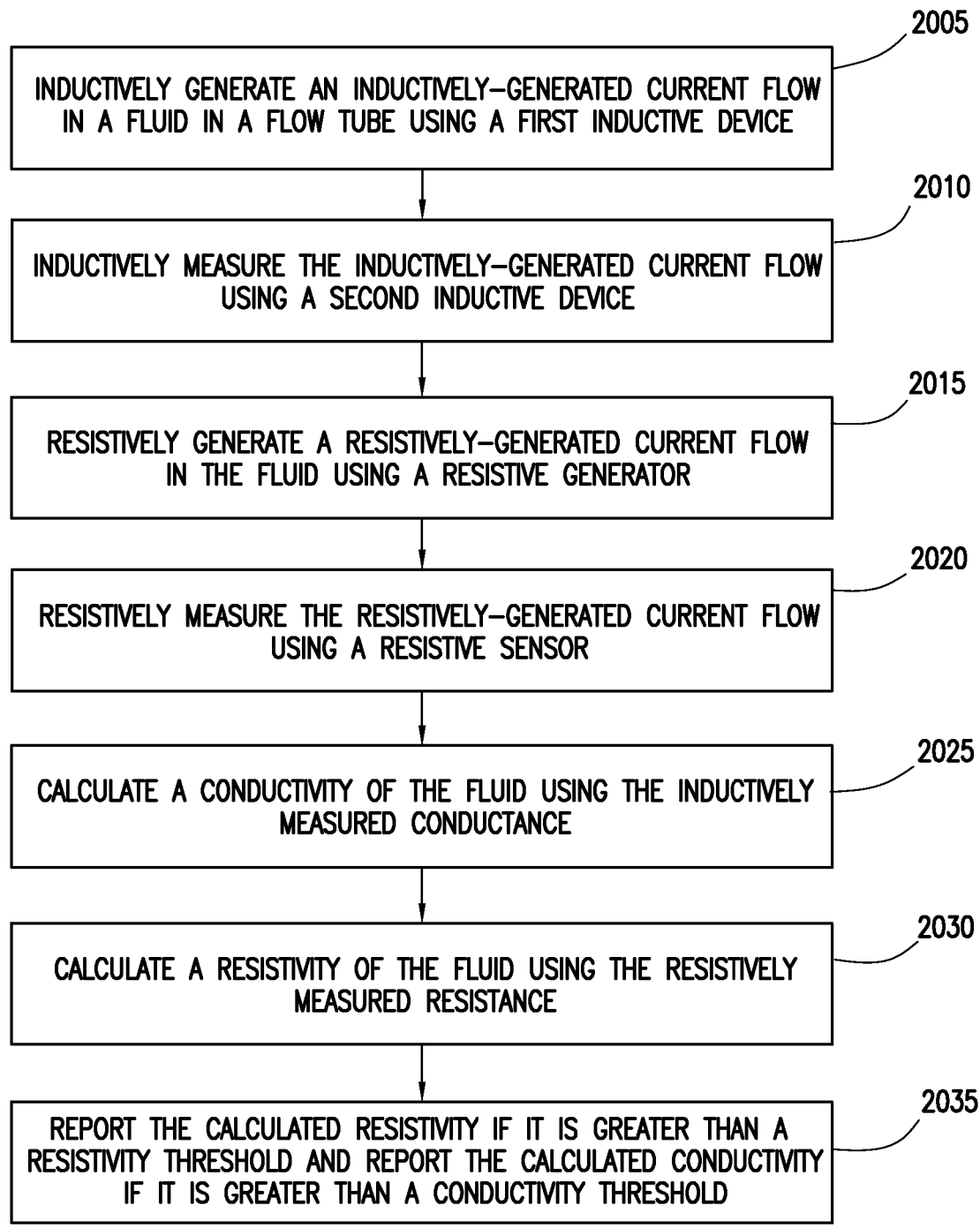

In one embodiment, illustrated in FIG. 20, an inductively-generated current flow is generated in a fluid in a flow tube using a first inductive device (block 2005), such as current injector 220. In one embodiment, the inductively-generated current flow is inductively measured using a second inductive device (block 2010), such as the current receiver 225. In one embodiment, a resistively-generated current flow in the fluid using a resistive generator (block 2015), such as the resistance measurement device 305. In one embodiment, the resistively-generated current flow is resistively measured using a resistive sensor (block 2020), such as the resistance measurement device 305. In one embodiment, a conductivity of the fluid is calculated using the inductively measured conductance (block 2025) by processor 235 using the methods described above with respect to FIGS. 16 and 17. In one embodiment, a resistivity of the fluid is calculated using the resistively measured current (block 2030), by processor 235 using the methods described above with respect to FIGS. 18 and 19.

In one embodiment, the processor 235 reports the calculated resistivity if it is greater than a resistivity threshold and reports the calculated conductivity if it is greater than a conductivity threshold. In one embodiment, (conductivity threshold)=1/(resistivity threshold).

In one embodiment, the processor 235 determines that the calculated conductivity is below the conductivity threshold and, in response, reports the calculated resistivity of the fluid.

In one embodiment, the processor 235 determines that the calculated resistivity is below a resistivity threshold and, in response, reports the calculated conductivity of the fluid.

In one embodiment, the processor 235 reports the calculated resistivity and the calculated conductivity.

Figure 21:
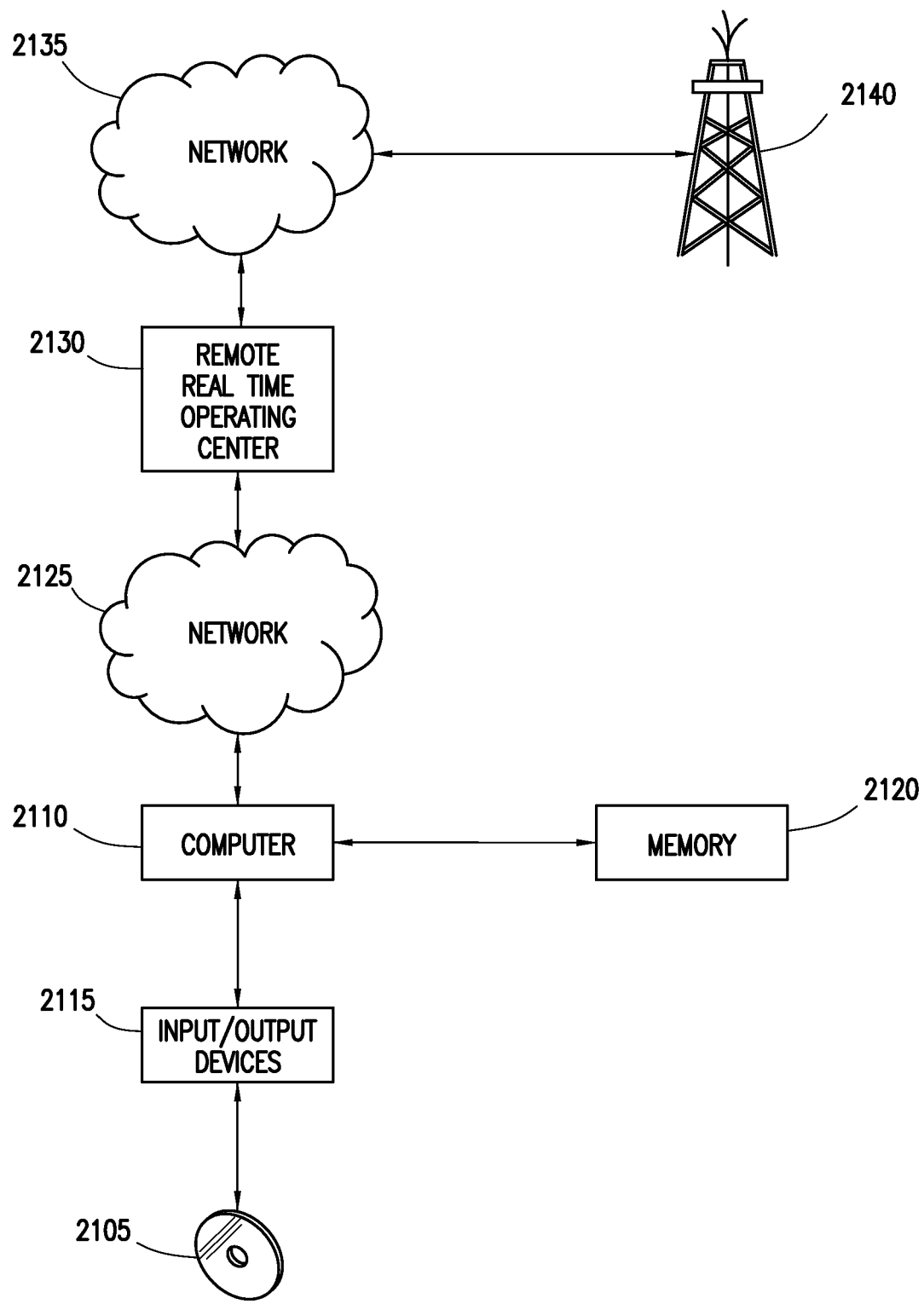
FIG. 21 illustrates an environment.

In one embodiment, shown in FIG. 21, the formation testing tool 135 is controlled by software in the form of a computer program on a non-transitory computer readable media 2105, such as a CD, a DVD, a USB drive, a portable hard drive or other portable memory. In one embodiment, a processor 2110, which may be the same as or included in the processor 235, reads the computer program from the computer readable media 2105 through an input/output device 2115 and stores it in a memory 2120 where it is prepared for execution through compiling and linking, if necessary, and then executed. In one embodiment, the system accepts inputs through an input/output device 2115, such as a keyboard or keypad, mouse, touchpad, touch screen, etc., and provides outputs through an input/output device 2115, such as a monitor or printer. In one embodiment, the system stores the results of calculations in memory 2120 or modifies such calculations that already exist in memory 2120.

In one embodiment, the results of calculations that reside in memory 2120 are made available through a network 2125 to a remote real time operating center 2130. In one embodiment, the remote real time operating center 2130 makes the results of calculations available through a network 2135 to help in the planning of oil wells 2140 or in the drilling of oil wells 2140.

The word "coupled" herein means a direct connection or an indirect connection.

The text above describes one or more specific embodiments of a broader invention. The invention also is carried out in a variety of alternate embodiments and thus is not limited to those described here. The foregoing description of an embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:
1. An apparatus comprising:
a helical flow tube in a formation testing tool;

a current injector to inject an electromagnetic current into the flow tube, wherein the current injector has two electrodes that extend into the flow tube;
a receiver coil positioned to produce a receiver coil signal in response to the electromagnetic current; and
a processor coupled to the receiver coil to calculate a conductivity of a fluid flowing through the flow tube based on the receiver coil signal;
wherein the processor calculates the conductivity of the fluid flowing through the flow tube as a measurement of the receiver coil signal in a complex domain multiplied by a real valued tool constant after a tool body signal is subtracted.

2. The apparatus of claim 1 wherein:
the receiver coil comprises a coil of wire in an insulating liner.

3. The apparatus of claim 1 further comprising:
a measurement circuit to receive the receiver coil signal; and
the measurement circuit to provide to the processor:
 an amplitude signal representing the amplitude of the receiver coil signal; and
 a phase signal representing the phase of the receiver coil signal.

4. An apparatus comprising:
a helical flow tube in a formation testing tool;
exactly one transmitter coil;
a receiver coil;
a resistance measurement device to measure a resistance of a fluid flowing through the flow tube; and
a processor;
wherein the transmitter coil, receiver coil, and processor are interconnected in such a way that the processor can calculate a conductivity of a fluid flowing through the helical flow tube,
wherein the transmitter coil and the receiver coil are a conductance measurement device to measure a conductance of the fluid flowing through the flow tube, and
wherein the processor reports a measurement of the resistance measurement device when the resistance of the fluid flowing through the flow tube is above a resistance threshold, and reports a measurement of the conductance measurement device when the conductance of the fluid flowing through the flow tube is above a conductance threshold.

5. The apparatus of claim 4 wherein:
the receiver coil comprises a coil of wire in an insulating liner.

6. The apparatus of claim 4 wherein:
the transmitter coil is coaxial with the receiver coil.

7. The apparatus of claim 4 wherein:
the processor reporting the measurement by the conductance measurement device of the conductance, $\sigma$, of the fluid includes the processor calculating:

$$\sigma = \frac{V}{K},$$

where:
V is a voltage measured at the receiver coil, $$K = \frac{N_T N_R I_T (\pi a^2)^2 \omega^2 \mu^2}{4\pi L},$$

$N_T$ is the number of turns in the transmitter coil,
$N_R$ is the number of turns in the receiver coil,
$I_t$ and $\omega$ are the amplitude and angular frequency, respectively, of a time harmonic current generated in the transmitter coil,
a is the radius of the transmitter coil and the receiver coil,
$\mu$ is the permeability of the formation, and
L is the distance between transmitter coil and the receiver coil.

8. The apparatus of claim 4 wherein:
the processor reporting the measurement by the resistance measurement device of the resistance, $\rho$, of the fluid, includes the processor calculating:

$\rho = RG$, where:

$$R = \frac{I}{V},$$

V is the voltage measured across a first electrode and a second electrode inserted in the fluid,
I is the current measured flowing through the fluid between the first electrode and the second electrode, and
G is a geometry factor determined during a calibration of the resistance measurement device.

9. The apparatus of claim 4 wherein:
the resistance measurement device comprises an electrode extending into the flow tube.

10. A method comprising:
inductively generating an inductively-generated current flow in a fluid in a flow tube using a first inductive device;
inductively measuring the inductively-generated current flow using a second inductive device;
resistively generating a resistively-generated current flow in the fluid using a resistive generator;
resistively measuring the resistively-generated current flow using a resistive sensor;
calculating with a processor in a downhole tool interconnected with the first inductive device and the second inductive device a conductivity of the fluid using the inductively measured current;
calculating with the processor interconnected with the resistive generator and the resistive sensor the resistivity of the fluid using the resistively measured current; and
wherein the processor reports the calculated resistivity when the calculated resistivity is above a resistance threshold and reports the calculated conductivity when the calculated conductivity is above a conductance threshold.

* * * * *